United States Patent [19]

Kawata

[11] Patent Number: 4,797,098
[45] Date of Patent: Jan. 10, 1989

[54] APPARATUS FOR DENTAL TREATMENT PROVIDED WITH CHECK VALVE IN FLUID PASSAGE

[75] Inventor: Shosaku Kawata, Kanuma, Japan

[73] Assignee: Nakanishi Dental Mfg. Co., Ltd., Japan

[21] Appl. No.: 41,090

[22] Filed: Apr. 22, 1987

[51] Int. Cl.⁴ .............................................. F27D 1/08
[52] U.S. Cl. .................................... 433/98; 222/571; 141/116; 137/614.2; 433/101
[58] Field of Search .................. 433/28, 98, 101, 100; 222/571; 141/116, 117, 119; 137/614.2

[56] References Cited

U.S. PATENT DOCUMENTS 2,982,446  5/1961  Lio Lios et al. ................... 222/571
4,062,480 12/1977  Bjorklund .......................... 222/571

Primary Examiner—Larry Jones
Assistant Examiner—Noah Kamen
Attorney, Agent, or Firm—Charles E. Baxley

[57] ABSTRACT

A dental treatment apparatus includes a pressurized fluid source for pressurizing and supplying a fluid necessary for performing dental treatment operation and fluid conduits for conveying the pressurized fluid. The pressurized fluid source and a handpiece communicate with each other by the fluid conduits and a valving member is interposed in the liquid conduit for sucking the liquid during in a direction opposite to the liquid supply direction when the dental treatment operation is terminated. A check valve is interposed in the liquid conduit between the valving member and the dental treatment tool provided at the extreme end of the dental handpiece.

4 Claims, 3 Drawing Sheets

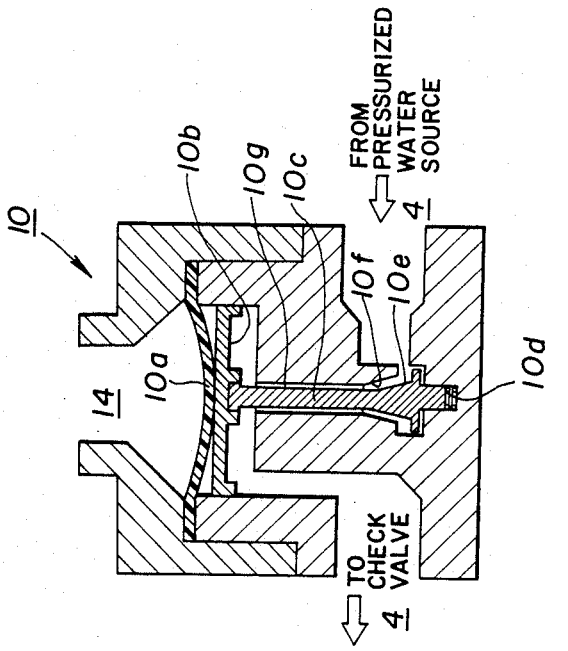
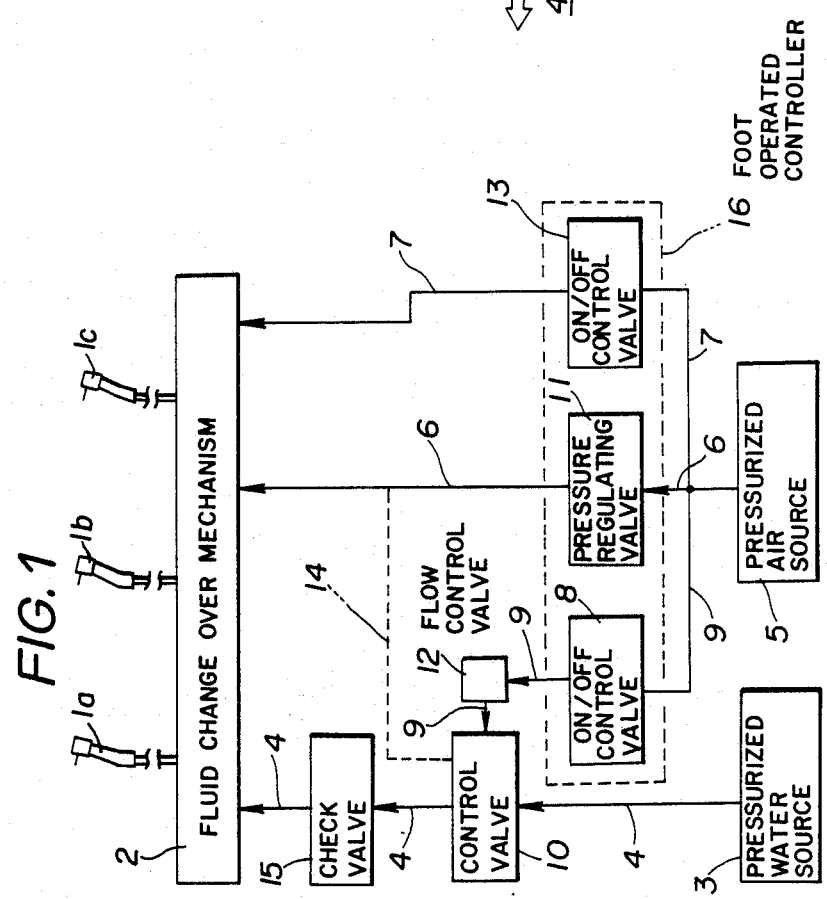

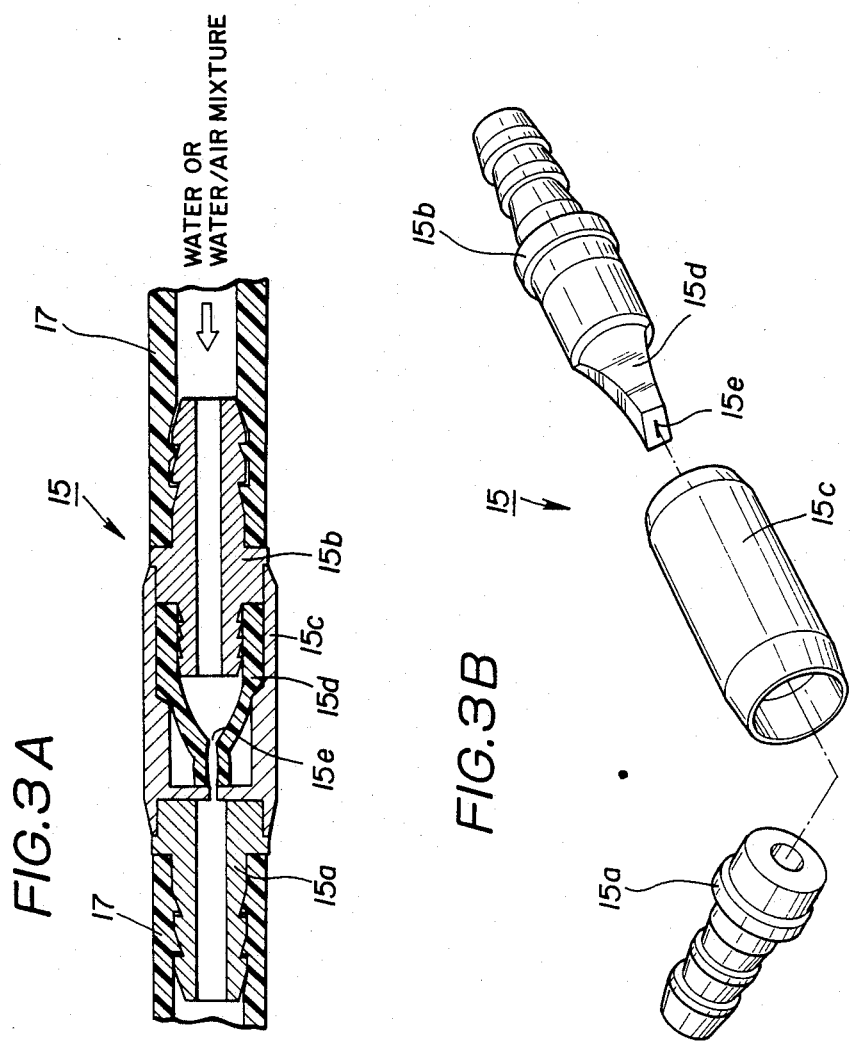

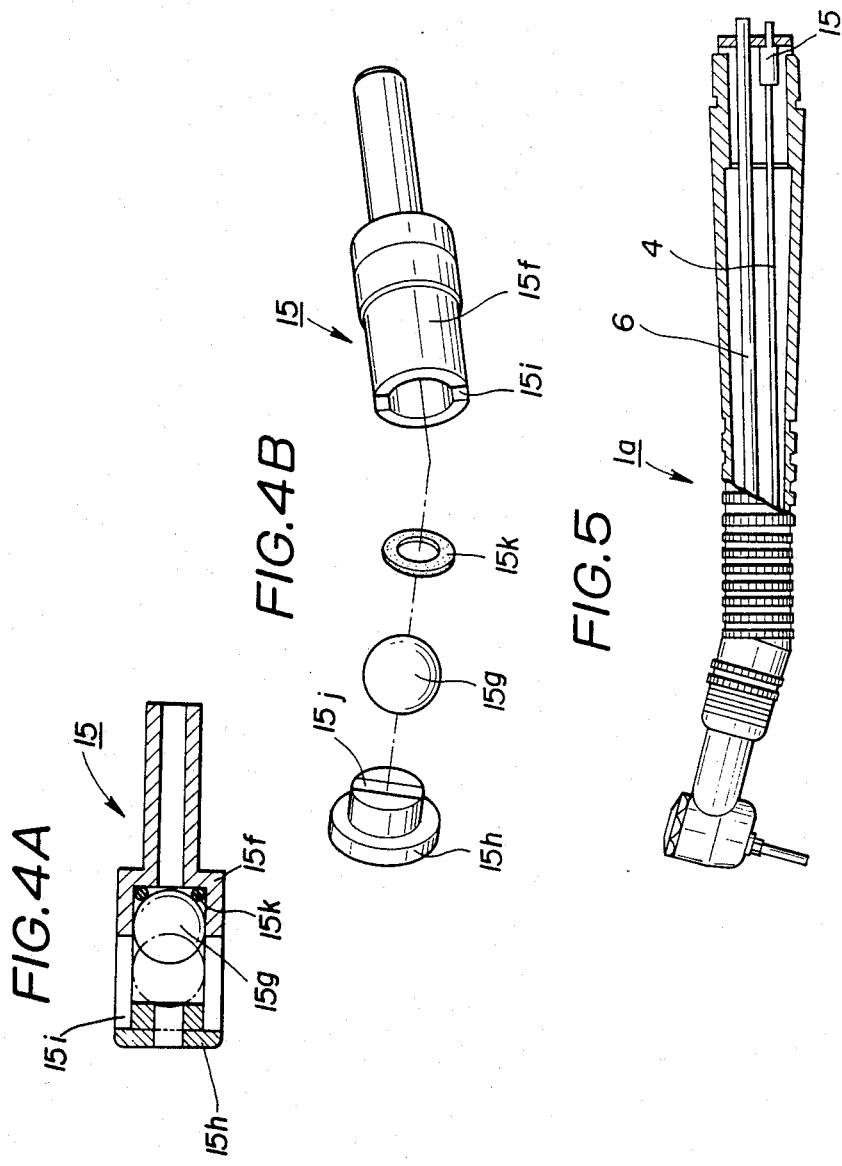

APPARATUS FOR DENTAL TREATMENT PROVIDED WITH CHECK VALVE IN FLUID PASSAGE

BACKGROUND OF THE INVENTION

1. Field of the Invention

This invention relates to a dental treatment apparatus provided with a check valve in a fluid passage thereof and, more particularly, to a dental treatment apparatus provided with a check valve for minimizing the fluid suction to be caused when terminating the dental treatment operation.

2. Related Art Statement

In currently used dental treatment apparatuses, there is included a fluid suction device such as a pull-back control valve having the function to pull back the pressurized fluid to suck the fluid so as to prevent the fluid from flowing down at the extreme end of the handpiece when the supply of the pressurized fluid is terminated. However, since this suction device sucks up about 1 ml of air, the patient's saliva and cut chips produced by the cutting tool provided to the dental handpiece are sucked simultaneously so as to be then discharged into the next patient's oral cavity. This is not only undesirable from the viewpoint of hygienics but also may give rise to cloging of the water supply passage.

OBJECTS AND SUMMARY OF THE INVENTION

It is a principal object of the present invention to provide a dental treatment apparatus in which the amount of air sucked during cessation of dental treatment is reduced substantially to nil so as to prevent suction of the patient's saliva, cut chips and the like.

It is another object of the present invention to provide a dental treatment apparatus in which the patient's saliva, cut chips and the like are not sucked so as to prevent cloging of fluid passages in the apparatus.

It is another object of the present invention to provide a dental treatment apparatus in which the patient's saliva, cut chips and the like are not sucked so as to prevent rusting of fluid passages otherwise caused by the action of the sucked materials.

It is a further object of the present invention to provide a dental treatment apparatus provided with a check valve device simple in manufacture and low in production costs.

The above and other objects of the invention will become apparent from the following description when taken in conjunction with the accompanying drawings.

According to the present invention, there is provided a dental treatment device comprising:

a pressurized fluid source for pressurizing and supplying fluid to perform dental treatment operation;

fluid passage means for supplying the fluid pressurized to a dental treatment tool provided to the extreme end of a dental handpiece;

suction means interposed between the pressurized fluid source and the handpiece and adapted to stop the flow of the pressurized fluid and to suck the fluid in a direction oposite to a supplying direction of the fluid when the dental treatment operation is terminated; and check valve means interposed in the fluid passage means between the suction means and the dental treatment tool and adapted to permit the pressurized fluid to pass through the dental treatment tool during supply of the pressurized fluid and to stop the flow of the fluid in the direction opposite to the supplying direction on terminating the dental treatment operation.

BRIEF DESCRIPTION OF THE DRAWINGS

FIG. 1 is a block view schematically showing a fluid circuit of the dental treatment apparatus according to the present invention;

FIG. 2 is a sectional view showing a control valve adapted to suck the fluid when the dental treatment operation is terminated;

FIG. 3A is a sectional view showing an embodiment of a check valve adapted for minimizing fluid suction when the dental treatment operation is terminated;

FIG. 3B is an exploded perspective view showing the check valve shown in FIG. 3A;

FIG. 4A is a sectional view showing another embodiment of the check valve;

FIG. 4B is an exploded perspective view of the check valve shown in FIG. 4A; and FIG. 5 is a side elevation showing the check valve of FIGS. 4A and 4B attached to the dental handpiece, with portions being cut away.

PREFERRED EMBODIMENTS OF THE INVENTION

FIG. 1 shows an overall schematic construction of a fluid circuit of a dental treatment apparatus according to the present invention. In FIG. 1, there is shown a fluid change over mechanism 2 connected to dental handpieces 1a, 1b and 1c. Pressurized rinsing water is supplied to this fluid change over mechanism 2 from a pressurized water source 3 through a water conduit 4 by way of a control valve 10 and a check valve 15. Pressurized air can be selectively supplied to the control valve 10 from a pressurized air source 5 through an air conduit 9 by way of an on/off control valve 8 and a flow control valve 12 so that an air/water mixture is supplied through the water conduit 4 to the fluid change over mechanism 2. A second air conduit 6 is connected by way of a pressure regulating valve 11 to the pressurized air source 5 for supplying the pressurized air for driving an air turbine, not shown, of the dental handpiece to the fluid change over mechanism 2. A third air conduit 7 is connected to the pressurized air source 5 through a second on/off control valve 13 for supplying to the fluid change over mechanism 2 pressurized air for blowing off cut chips or food residua in the oral cavity. The on/off control valves 8, 13 and the pressure regulating valve 11 are controlled by a foot operated controller 16 controlled by the dentist's foot to optionally supply air, water or an air/water mixture to each of the dental handpieces 1a, 1b and 1c through the fluid change over mechanism 2 as the occasion may demand.

Referring to FIG. 2, the control valve 10 is shown in a schematic cross-section. The control valve 10 is connected by a bypass conduit 14 shown by a dotted line in FIG. 1 to the second air conduit 6 adapted for driving the air turbine. As long as the air turbine is driven by the pressurized air by way of the second air conduit 6, a rubber diaphragm 10a is biased under the air pressure as shown in FIG. 2 so that an abutment plate member 10b in abutment with the diaphragm 10a is thereby lowered. This results in the abutment plate member 10b lowering an abutment rod 10c against the force of a spring 10d.

The abutment rod 10c has a tapered portion 10e and, when the rubber diaphragm 10a is not biased by the air pressure, the abutment rod 10c is raised by the spring 10d, so that the tapered portion 10e fits into a complementary tapered portion 10f, thereby interrupting communication of the water conduit 4. When the diaphragm 10a is placed under the pressure as shown, the conduit 4 permits water or an air/water mixture to be freely circulated through grooves 10g.

When the dentist operates the foot-operated controller 16 to close the pressure regulating valve 11 to terminate the supply of the pressurized air through the second air conduit 6 and hence to stop the cutting of the teeth, the rubber diaphragm 10a is freed of the pressure from the bypass conduit 14 so that the diaphragm 10a is returned to its flat state by its own resiliency. The water or the air/water mixture in the water conduit 4 including the water conduit 4 within the handpieces 1a, 1b and 1c, see FIG. 5, is drawn by suction, as soon as the control valve 10 is closed by the tapered portions 10e, 10f mating with each other, as described above. When employing the pull-back type control valve 10, there is an advantage that no water will flow down from the end of the handpiece upon terminating the dental treatment operation, but there is a disadvantage that saliva or cut chips are sucked at this time. According to the present invention, the check valve 15 is interposed between the control valve 10 and the end parts of the handpieces 1a, 1b and 1c for eliminating such inconvenience.

An embodiment of the check valve 15 is shown in FIGS. 3A and 3B. The check valve 15 is adapted to be connected to hose sections 17 constituting the aforementioned water conduit 4. The check valve 15 is comprised of a front inserting tube section 15a having stepped portions to inhibit extrication from the associated hose section 17, a rear inserting tube section 15b having similar stepped portions and a central connecting section 15c interconnecting these inserting tube sections 15a and 15b. A resilient valving member 15d formed of a resilient material such as rubber or synthetic resin is fitted into the inside of the central connecting portion 15c as shown. Thus, the valving member 15d is in the form of a cup, the base part of which has a through-slit 15e in communication with the bore of the front inserting tube section 15a and the flared open end of which is clamped between the terminus of the connecting section 15b. The pressurized water or the pressurized air/water mixture supplied in the direction of an arrow in FIG. 3A causes the valving member 15d to be extended while also causing the through-slit 15e to be opened so that the water or the air/water mixture will flow into the bore of the front inserting tube section 15a. When the pressure is released, the resilient valving member 15d is resiliently contracted to close the through-slit 15e, as shown in FIG. 3B.

A modified embodiment of the check valve 15 is shown in FIGS. 4A and 4B. The check valve 15 shown therein is comprised of a tubular member 15f, a ball valve 15g and a valve seat 15h. During the time the pressurized water or air/water mixture is circulated, the ball valve 15g abuts on the valve seat 15h, as indicated by the chain dotted line in FIG. 4A, the water or the air/water mixture then being circulated through a groove 15i formed in the tubular member 15f and a groove 15j formed in the valve seat 15h. When the pressure is released so that the water or the water/air mixture is drawn by suction by the control valve 10, the ball valve 15g is returned to the solid line position shown in FIG. 4A into abutment with a ring 15k to close the check valve 15.

The check valve 15 shown in FIGS. 4A and 4B is adapted to be enclosed in the rear extremity of the water conduit 4 of the handpiece 1a, as shown in FIG. 5. The numeral 6 denotes an air conduit for driving the air turbine, not shown.

According to the present invention, since the check valve 15 shown in FIGS. 3A, 3B, 4A and 4B is provided in the water conduit 4 including the water conduit 4 in the handpiece 1a to 1c, the amount of suction through the control valve 10 may be reduced to as low as approximately 0.008 ml, so that it becomes possible to reduce the suction of saliva, cut chips and the like from the end of the handpiece to an extremely small value, while preventing the water from flowing down during cessation of the dental treatment operation.

Although the present invention has been described with reference to the preferred embodiments, it should be understood that various modifications and variations can be easily be made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A dental treatment apparatus comprising:
   a pressurized fluid source for pressurizing and supplying fluid to perform dental treatment operation;
   fluid passage means for supplying said fluid pressurized to a dental treatment tool provided to the extreme end of a dental handpiece;
   suction means interposed between said pressurized fluid source and said handpiece and adapted to stop the flow of said pressurized fluid and to suck the fluid in a direction opposite to a supplying direction of said fluid when said dental treatment operation is terminated; and
   check valve means interposed in said fluid passage means between said suction means and said dental treatment tool, said check valve means including a resilient valving member and a through-slit formed in said valving member, said slit being extended apart under pressure to permit the fluid to pass therethrough when said pressurized fluid is conveyed through said check valve means during said dental treatment operation, said through-slit being closed by the resiliency of said valving member to inhibit the fluid lying between the check valve and the dental treatment tool from being sucked towards said suction means when said dental treatment operation is terminated.

2. A dental treatment apparatus according to claim 1 wherein said check valve means is provided to a hose forming said fluid passage means.

3. A dental treatment apparatus according to claim 1 wherein said check valve means is provided to said dental handpiece having the fluid passage means enclosed therein.

4. A dental treatment apparatus according to claim 1 wherein said suction means includes a valving member communicating with a conduit for a pressurized gas adapted to drive a dental treatment tool for cutting teeth, said valving member being opened and closed under the pressure, said check valve means being actuated on closure of said valving member for stopping the flow of fluid including at least a liquid.

* * * * *